(12) United States Patent
Clerc et al.

(10) Patent No.: US 11,026,820 B2
(45) Date of Patent: *Jun. 8, 2021

(54) STENT DELIVERY DEVICE

(71) Applicant: BOSTON SCIENTIFIC SCIMED, INC., Maple Grove, MN (US)

(72) Inventors: Claude O. Clerc, Marlborough, MA (US); Jonathan Root, Groveland, MA (US); Tewodros Admassu, Malden, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 588 days.

This patent is subject to a terminal disclaimer.

(21) Appl. No.: 15/871,451

(22) Filed: Jan. 15, 2018

(65) Prior Publication Data
US 2018/0133041 A1 May 17, 2018

Related U.S. Application Data

(63) Continuation of application No. 13/937,751, filed on Jul. 9, 2013, now Pat. No. 9,883,958.
(Continued)

(51) Int. Cl.
*A61F 2/95* (2013.01)
*A61F 2/962* (2013.01)
(Continued)

(52) U.S. Cl.
CPC .............. *A61F 2/95* (2013.01); *A61F 2/9517* (2020.05); *A61F 2/962* (2013.01); *A61B 2017/0042* (2013.01); *A61F 2002/0072* (2013.01)

(58) Field of Classification Search
CPC .. A61F 2/95; A61F 2/9517; A61F 2/01; A61F 2/013; A61F 2002/0072;
(Continued)

(56) References Cited

U.S. PATENT DOCUMENTS

| 5,415,664 A | 5/1995 | Pinchuk |
| 6,629,981 B2 | 10/2003 | Bui et al. |

(Continued)

FOREIGN PATENT DOCUMENTS

| WO | 0002503 A1 | 1/2000 |
| WO | 2012078794 A1 | 6/2012 |

OTHER PUBLICATIONS

Notification of Transmittal of the International Search Report and the Written Opinion of the International Searching Authority, or the Declaration for PCT/US2013/049874 dated Nov. 14, 2013 (9 pgs).

*Primary Examiner* — Tan-Uyen T Ho
*Assistant Examiner* — Rachel S Highland
(74) *Attorney, Agent, or Firm* — Seager, Tufte & Wickhem, LLP (57) ABSTRACT

A stent delivery device has a handle and a sliding body, the sliding body is slidable with respect to the handle. The handle has a grip and a guide. The sliding body has at least two flange portions extending from the sliding body. The flange portions are offset from one another along the length of the sliding body. The operator can thereby deploy a relatively long stent by first gripping the nearest flange portion and pulling the sliding body toward the handle; subsequently, the operator can reposition his/or finger on the next-nearest flange portion and continue deployment of the stent by pulling the sliding body further toward the handle.

19 Claims, 7 Drawing Sheets

Related U.S. Application Data (60) Provisional application No. 61/672,068, filed on Jul. 16, 2012.

(51) Int. Cl.
  *A61B 17/00* (2006.01)
  *A61F 2/00* (2006.01)

(58) Field of Classification Search
  CPC . A61F 5/0089; A61B 17/12; A61B 17/12009; A61B 2017/12018; A61B 17/00; A61B 2017/0042; A61B 2002/0072
  See application file for complete search history.

(56) References Cited

U.S. PATENT DOCUMENTS

| | | |
|---|---|---|
| 7,635,382 B2 | 12/2009 | Pryor |
| 2006/0258972 A1 | 11/2006 | Mangiardi et al. |
| 2006/0271064 A1 | 11/2006 | Agnew |
| 2007/0100421 A1 | 5/2007 | Griffin et al. |
| 2009/0118740 A1 | 5/2009 | Mangiardi et al. |
| 2009/0192518 A1 | 7/2009 | Golden et al. |
| 2010/0049295 A1 | 2/2010 | Satasiya et al. |

STENT DELIVERY DEVICE

CROSS-REFERENCE TO RELATED APPLICATIONS

This Application is a continuation of U.S. application Ser. No. 13/937,751, filed Jul. 9, 2013, which claims priority to and the benefit of U.S. Provisional Application No. 61/672,068, filed Jul. 16, 2012, the entire contents of which are herein incorporated by reference.

STATEMENT REGARDING FEDERALLY SPONSORED RESEARCH

Not Applicable

BACKGROUND OF THE INVENTION

Various types of stents and stent deployment devices are known in the art. In particular, stents of the self-expanding and balloon expandable varieties and devices for deploying such stents are used to repair blood vessels, arteries, fluid passages, airways, gastrointestinal tracts, and other bodily lumens.

In some instances, it is desirable to use a stent that is relatively long, for example 100 mm in length. Relatively long stents can be more difficult to deploy than their shorter counterparts. Additionally, delivery devices requiring two hands to operate can be cumbersome. Consequently, there remains a need for a stent delivery device that is capable of effectively delivering relatively long stents to body lumens. There further remains a need for such a delivery device that can be operated with a single hand.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In some embodiments, a stent delivery device comprises a handle and a sliding body. The handle has a grip, a guide, and a protruding member. Further, the handle defines a cavity and the protruding member extends into the cavity. The sliding body comprises a guide surface. The sliding body further comprises a plurality of flange portions. In some embodiments, the flange portions are longitudinally offset from one another. The guide surface is slidably engaged to the guide and the sliding body is slidable over the protruding member.

In some embodiments, the guide defines a channel. Moreover, in some embodiments, the sliding body comprises a ridge and the ridge has a guide surface thereon.

In some embodiments, the guide comprises a ridge and the sliding body defines a channel. In some embodiments, the channel further defines a guide surface.

In some embodiments, the handle comprises a first guide and a second guide and the sliding body comprises a first ridge and a second ridge. The first ridge is slidably engaged to the first guide and the second ridge is slidably engaged to the second guide.

In some embodiments, the first ridge is opposed the second ridge.

In some embodiments, the sliding body defines a cavity and the protruding member is insertable into the cavity.

In some embodiments, the protruding member defines a hole extending therethrough.

In some embodiments, the sliding body has two flange portions.

In some embodiments, the sliding body has four flange portions.

In some embodiments, two of the flange portions are longitudinally offset from the other two flange portions.

In some embodiments, the grip comprises a pistol grip.

In some embodiments, the invention is directed to a delivery device for delivering a medical implant. The delivery device comprises a handle and a sliding body. The handle comprises a main body, a pistol grip, and a pair of arms extending from the main body. In some embodiments, each of the arms comprises a guide. In some embodiments, the sliding body comprises a plurality of guide surfaces and a plurality of flange portions. In some embodiments, the flange portions are longitudinally offset from one another and the guide surfaces are slidably engaged to the guides. In some embodiments, the sliding body defines a first hole extending therethrough and the handle defines a second hole extending therethrough. The first and second holes have a common longitudinal axis.

In some embodiments, the handle further comprises a protruding member and the second hole extends through the protruding member.

In some embodiments, the sliding body defines a cavity and the protruding member is insertable into the cavity.

In some embodiments, the delivery device has a first configuration and a second configuration. In the first configuration, the sliding body is in a first position; in the second configuration, the sliding body is in a second position. The second position is longitudinally offset from the first position.

In some embodiments, a delivery device for delivering a medical implant comprises a handle and a sliding body. In some embodiments, the handle defines a cavity and comprises a grip and at least one guide. The at least one guide extends from the handle. In some embodiments, the sliding body comprises a body portion and a plurality of flange portions. The flange portions extend from the body portion and are longitudinally offset from one another. In some embodiments, at least a portion of the sliding body is slidable along the at least one guide between an extended configuration and a retracted configuration.

DETAILED DESCRIPTION OF THE INVENTION

While this invention may be embodied in many different forms, there are described in detail herein specific embodiments. This description is an exemplification of the principles of the invention and is not intended to limit it to the particular embodiments illustrated.

For the purposes of this disclosure, like reference numerals in the figures shall refer to like features unless otherwise indicated.

Figure 1:
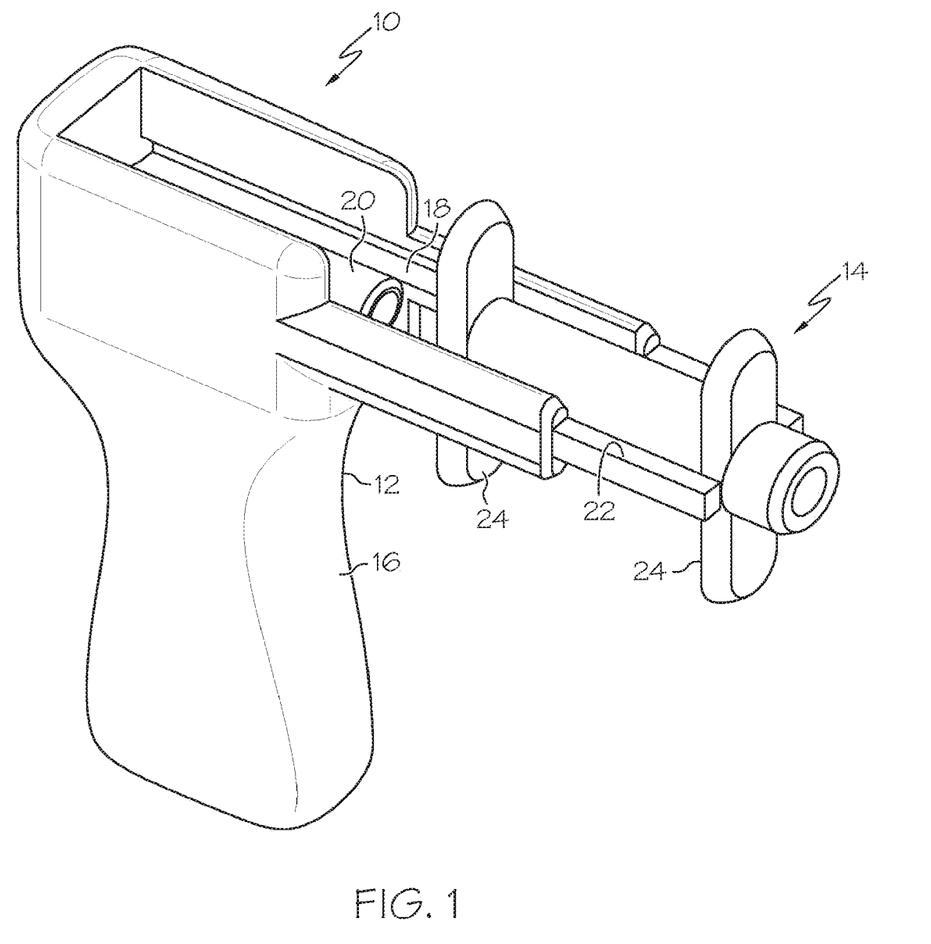
FIG. 1 shows a perspective view of an embodiment of a delivery device.

In at least one embodiment, for example as shown in FIG. 1, a stent delivery device 10 comprises a handle 12 and a sliding body 14. In some embodiments, the handle comprises a grip 16, a guide 18, and a protruding member 20. Further, in some embodiments, the sliding body 14 comprises a guide surface 22 and a plurality of flange portions 24. In some embodiments, the sliding body 14 comprises a plurality of guide surfaces 22.

In some embodiments, the guide surface 22 is slidably engaged to the guide 18 and the sliding body 14 is movable over the protruding member 20 such that the protruding member 20 extends into the sliding body 14.

Figure 2:
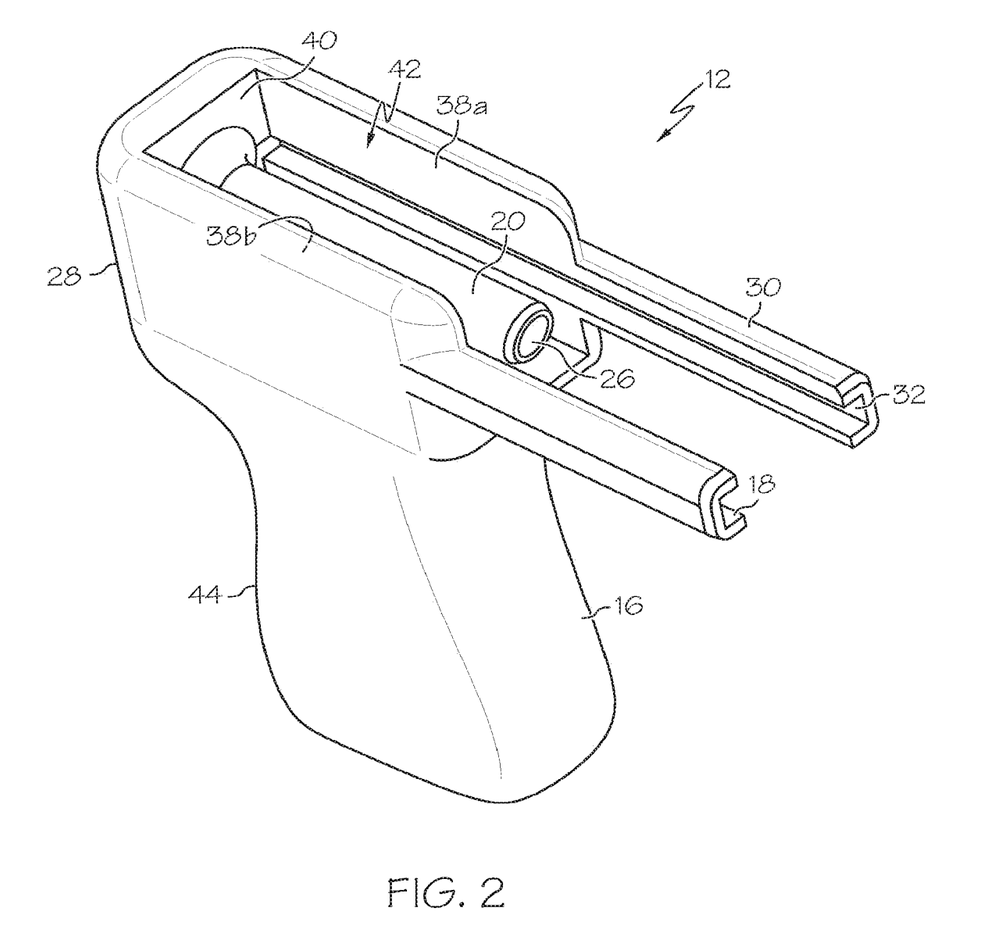
FIG. 2 shows a perspective view of the handle of the delivery device of FIG. 1.

Turning to FIG. 2, in some embodiments, the handle 12 further comprises a main body 28 and at least one arm 30 extending from the main body 28. As further shown in FIG. 2, in some embodiments, the handle 12 comprises two arms 30 extending from the main body 28. Further, the guides 18 extend along the at least a portion of the arms 30 and at least a portion of the main body 28. In some embodiments, the guides 18 extend along the entire length of one or more of the arms 30. In some embodiments, each of the guides 18 defines a channel 32.

In some embodiments, the handle 12 comprises a pistol grip 44. The pistol grip 44 allows the operator to ergonomically operate and maneuver the delivery device 10. Although shown in FIG. 2 with the pistol grip 44, other suitable configurations are also contemplated. Further, in some embodiments, the pistol grip 44 comprises a soft or tacky coating or polymer.

Figure 3:
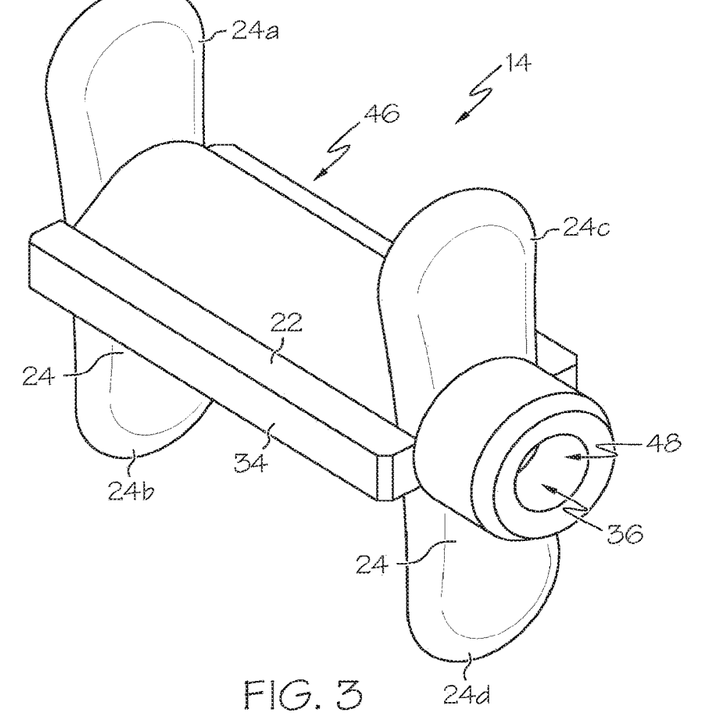
FIG. 3 shows a perspective view of the sliding body of the delivery device of FIG. 1.

With reference to FIG. 3, in some embodiments, the sliding body 14 comprises at least one ridge 34. The ridge 34, in turn, comprises the guide surface 22. In some embodiments, the ridge 34 comprises a plurality of guide surfaces 22. As shown in FIG. 3, the ridge 34 has three guide surfaces 22; each of the guide surfaces 22 is oriented at a right angle relative to the adjacent guide surface 22. The ridge 34 can comprise any suitable shape. For example, the ridge 34 can have two guide surfaces 22, forming a triangular cross-section. Moreover, the ridge 34 can have a rounded guide surface 22; the ridge 34 can be semi-circular, ovoid, or take on any other suitable configuration. Further, the ridge 34 can have any suitable number of guide surfaces 22.

In some embodiments, the sliding body 14 comprises a plurality of flange portions 24 extending therefrom. At least two of the flange portions 24 are longitudinally offset from one another. In some embodiments, the sliding body 14 has four flange portions 24, as shown in FIG. 3. Two of the flange portions 24a and 24b are diametrically opposed to one another and longitudinally offset from flange portions 24c and 24d, which are also diametrically opposed to one another. Of course, other suitable configurations, some of which are described in further detail below, are also contemplated. The flange portions 24 may be of any suitable size or shape. In some embodiments, the flange portions 24 may be sized to provide requisite leverage. The shape of the flange portions 24 is, in some embodiments, ergonomic.

In some embodiments, the flange portions 24 extend orthogonally from the sliding body 14, for example as shown in FIG. 3. Other configurations are also suitable. For example, the flange portions 24 can comprise a rounded trigger shape, similar to a firearm trigger. In some embodiments, the flange portions 24 have a concave portion. In some embodiments, the flange portions 24 comprise hoops around which the operator's fingers can be wrapped.

Figure 4A:
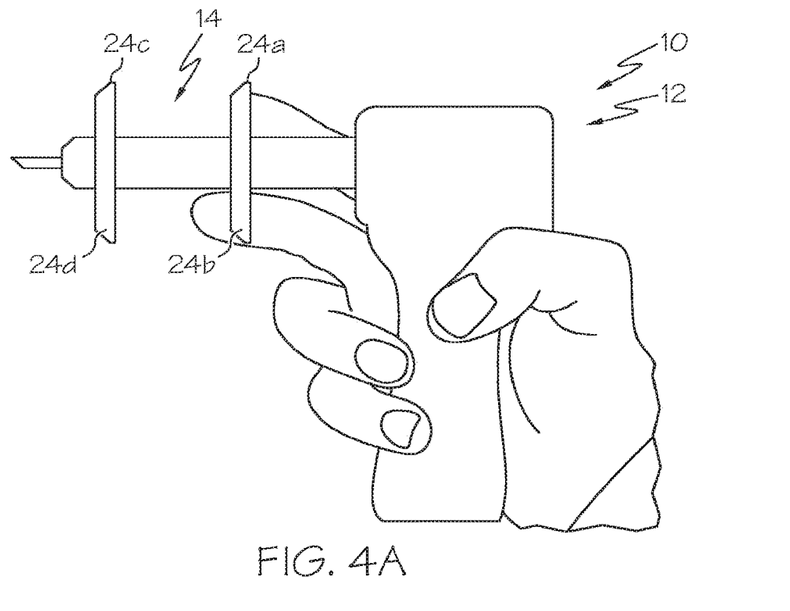
FIG. 4A shows the delivery device of FIG. 1 with the sliding body positioned away from the handle.
Figure 4B:
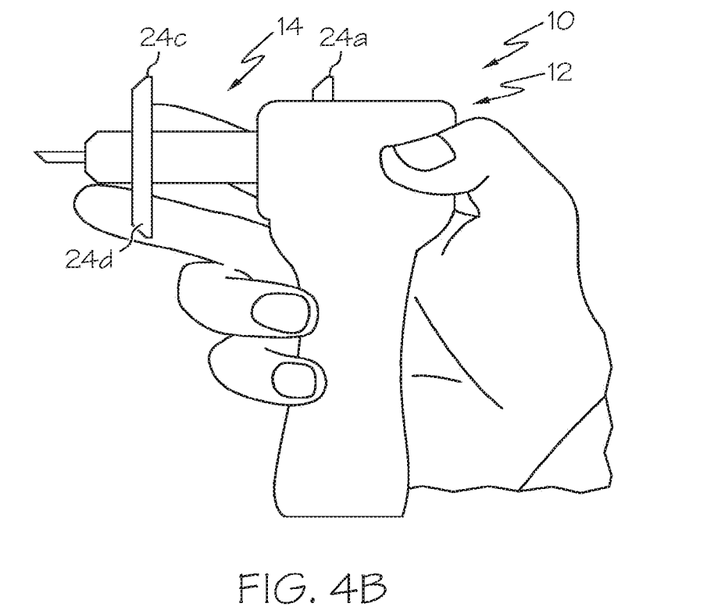
FIG. 4B shows the delivery device of FIG. 1 with the sliding body partially retracted.
Figure 4C:
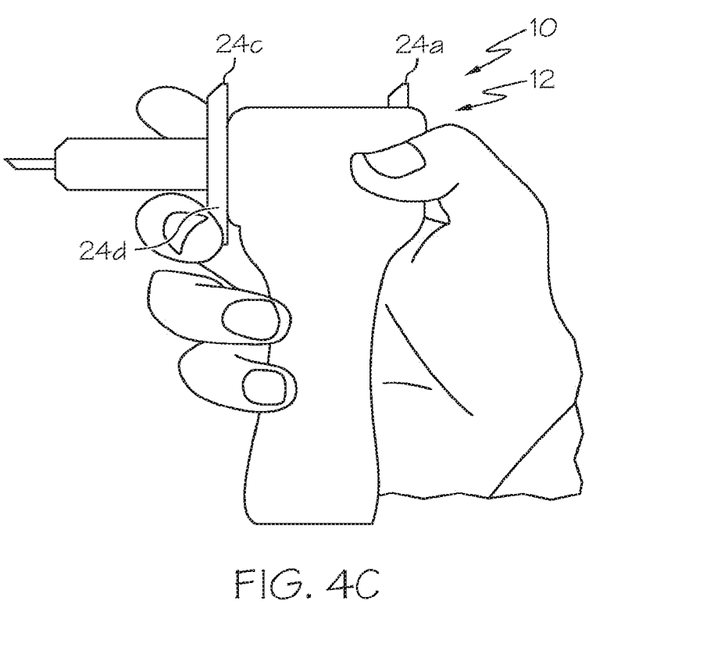
FIG. 4C shows the delivery device of FIG. 1 with the sliding body fully retracted.

Turning to FIGS. 4A-4C, an embodiment of the stent delivery device 10 is shown in various stages of retraction. In FIG. 4A, the sliding body 14 is positioned away from the handle 12. In FIG. 4B, however, the sliding body 14 is partially retracted. Finally, in FIG. 4C, the sliding body 14 is fully retracted. It will be appreciated that, in some embodiments, the sliding body 14 is attached to a sheath (not shown) which can be operably retracted to permit deployment of a stent (not shown). In particular, the delivery device 10 can be used with relatively long stents, for example up to 100 mm in length. Such stents are deployed in two steps. First, the operator grasps the proximal flange portions 24a and 24b, as shown in FIG. 4A, and retracts the sliding body 14 to the configuration shown in FIG. 4B. Thereafter, the operator repositions his/her fingers onto the distal flange portions 24c and 24d and continues retracting the sliding body 14 until the stent is fully deployed and/or the sliding body 14 is fully retracted, as shown in FIG. 4C. Depending upon the length of the stent to be deployed, the sliding body 14 can include any suitable number of flange portions 24. Further, in some embodiments, the delivery device 10 can be operated with one hand, thereby freeing the operator's other hand to perform another task, as necessary.

In some embodiments, the delivery device 10 is used to deliver airway stents into an airway passage, for example the trachea. In some embodiments, the delivery device is used to deliver a self-expanding stent. Moreover, in some embodiments, the delivery device can be used in combination with snares, ligator bands, sphincterotomes, retrieval baskets, clips, radiofrequency ablation needles, or any other suitable device requiring, for example, delivery or actuation.

Returning to FIG. 3, in some embodiments, the sliding body 14 defines a cavity 36 and a through-hole 48. Further, in some embodiments, the protruding member 20 of the handle 12 extends into the cavity 36 as the sliding body 14 is retracted towards the handle 12. In some embodiments, the protruding member 20 defines a hole 26 extending therethrough. A guidewire, dilator, or other device (e.g., balloon) (not shown), is permitted to pass through the hole 26 of the protruding member 20, for the purpose of guiding a catheter. Further, the guidewire is permitted to pass through the through-hole 48 of the sliding body 14. In some embodiments, the hole 26 of the protruding member 20 and the through-hole 48 of the sliding body 14 have a common longitudinal axis.

In some embodiments, the sliding body 14 comprises a body portion 46. In some embodiments, the proximal flange portions 24a, 24b are longitudinally coterminous with one or more of the guide surfaces 22 and the body portion 46. In some embodiments, at least a portion of the body portion 46 extends distally beyond the distal flange portions 24c, 24d and one or more of the guide surfaces 22, for example as shown in FIG. 3. Other configurations are also suitable.

Returning to FIG. 2, in some embodiments, the handle 12 comprises two opposing sides 38a, 38b and a back 40. In conjunction, the opposing sides 38a, 38b and the back 40 define a pocket 42. Upon fully retracting the sliding body 14 into the pocket 42, in some embodiments, one or more of the proximal flange portions 24a, 24b come into contact with the back 40. Consequently, in some embodiments, the back 40 prevents further retraction of the sliding body 14.

In some embodiments, the handle 12 comprises a frame without walls. Further, in some embodiments, the back 40 is a stop member to prevent retraction of the sliding body.

Figure 5:
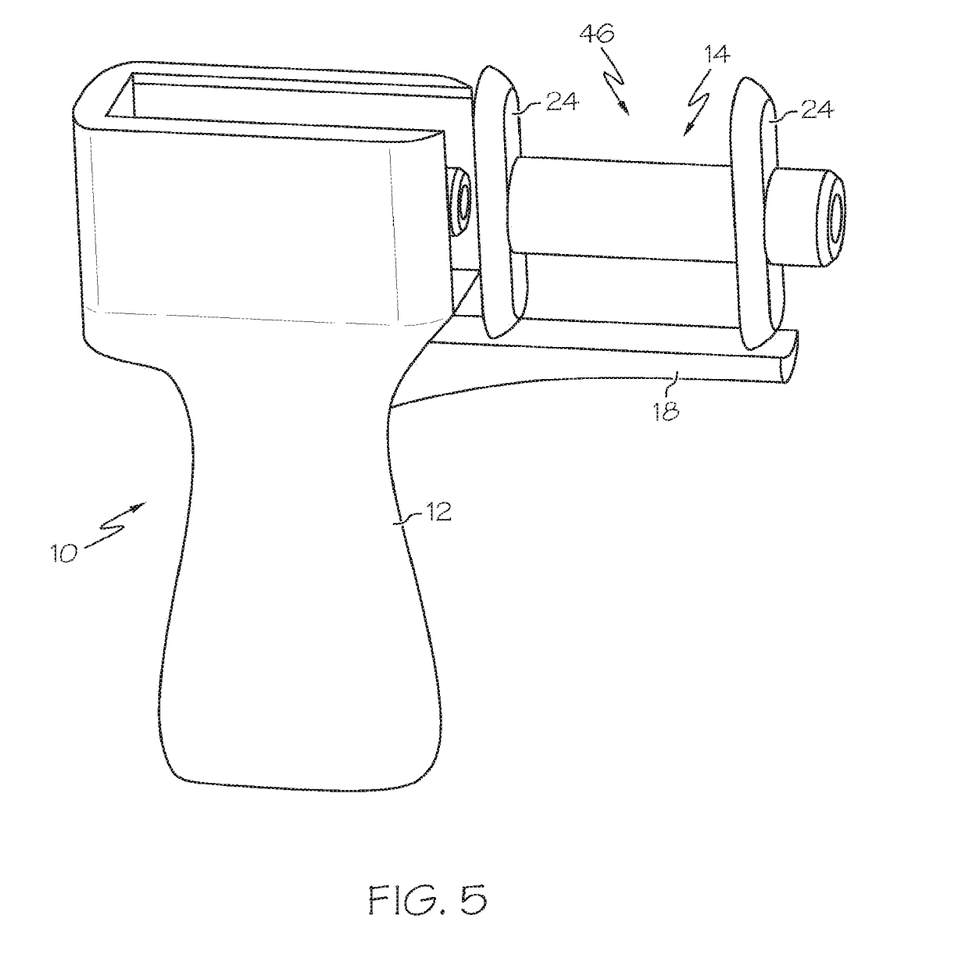
FIG. 5 shows a perspective view of an embodiment of the delivery device.

In addition to the foregoing, although the handle 12 of FIG. 2 has two guides 18 in opposing relationship to one another, it will be appreciated that the handle 12 can have only a single guide 18 or any suitable number of guides, for example three, four, or more. It will further be appreciated that the guide(s) 18 can be arranged in any suitable location. For example, where a single guide 18 is used, it can be oriented as shown in FIG. 5.

Figure 6:
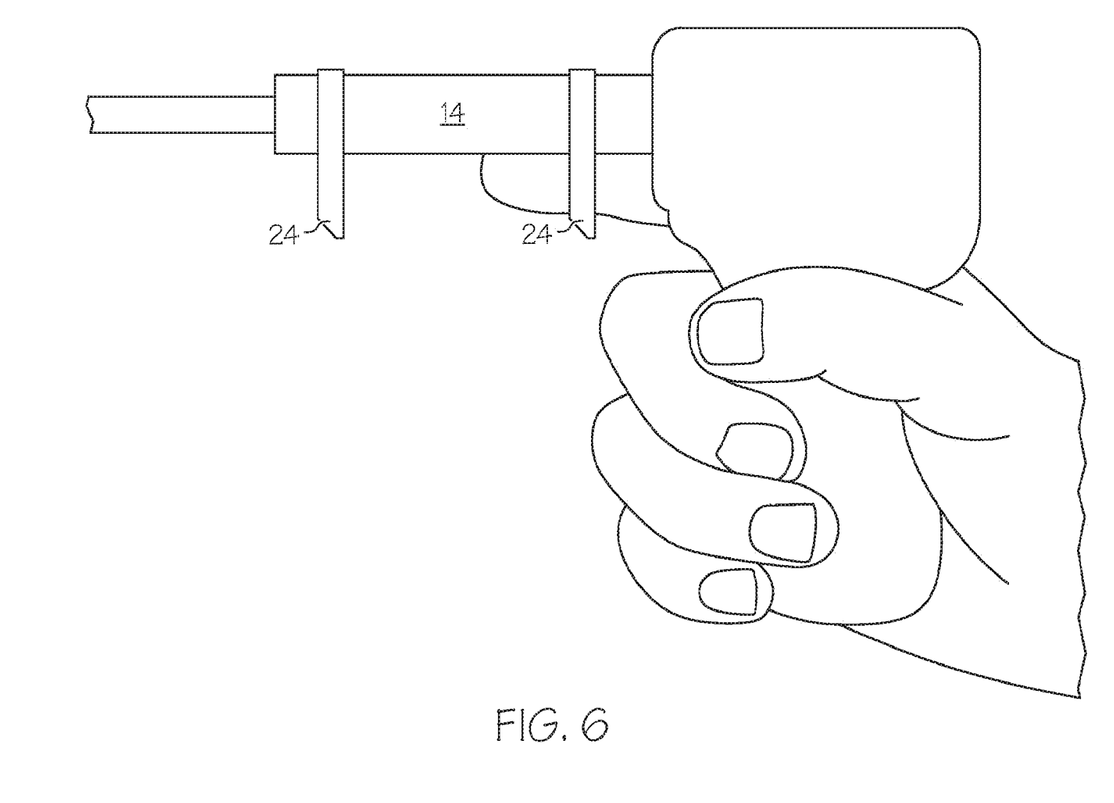
FIG. 6 shows a perspective view of an embodiment of the delivery device.

With regard to FIG. 6, in some embodiments, the sliding body 14 has flange portions 24 on only one side. In the embodiment of FIG. 6, retraction of the sliding body 14 can be performed using a single finger, for example an index finger. Deployment of a stent using the embodiment of FIG. 6 may be carried out in a fashion similar to that described above with respect to FIGS. 4A-4C, except that the operator need only use one finger.

Figure 7:
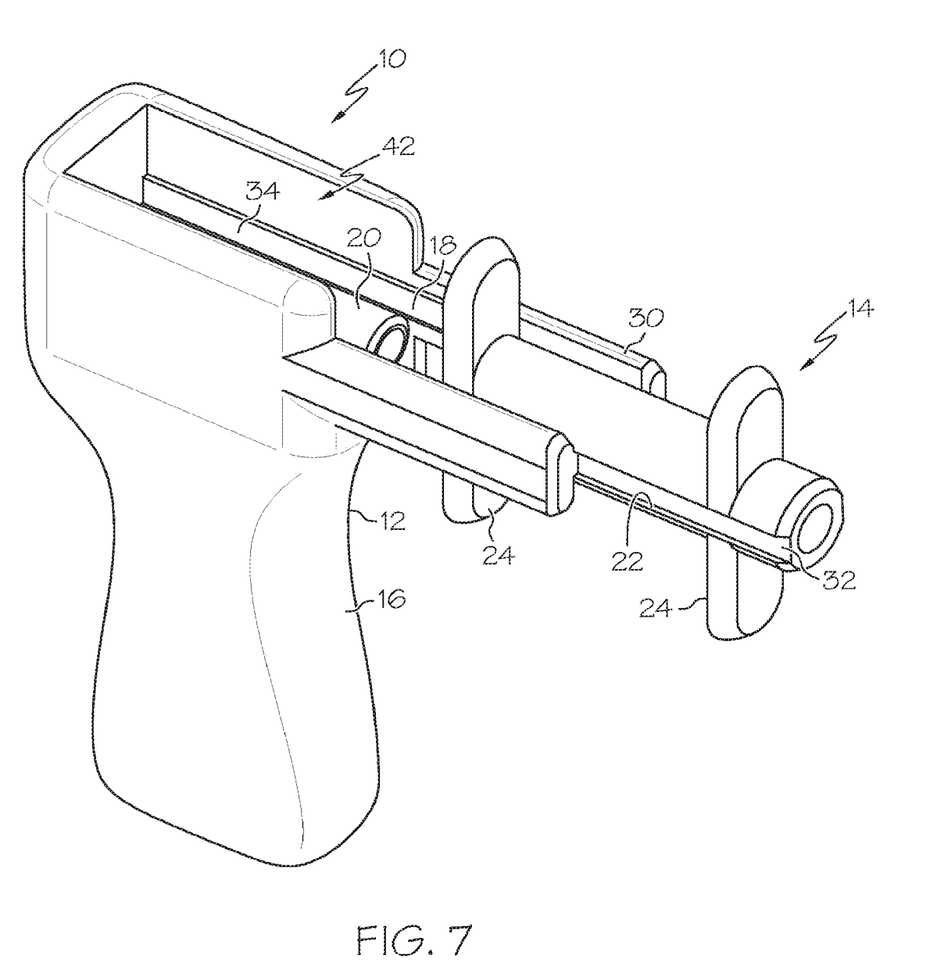
FIG. 7 shows a perspective view of an embodiment of a delivery device.

As shown in FIG. 7, in some embodiments, the guide(s) 18 extend(s) into the pocket 42 and the sliding body 14 has guide surfaces 22 which mate with the guide(s) 18. As further shown in FIG. 7, the guides 18 protrude from the arms 30, facing one another. Additionally, in some embodiments, the guide surfaces 22 which mate with the guides 18 are indentations along lateral sides of the sliding body 14.

As further shown in FIG. 7, in some embodiments, the guides 18 comprise ridges 34. In some embodiments, the ridges 34 are rails. Further, in some embodiments, the sliding body 14 defines a channel 32. In some embodiments, for example as shown in FIG. 7, the channel 32 defines at least one guide surface 22.

In light of the foregoing, it will be evident to the skilled artisan that the handle 12 and sliding body 14 can have any suitable interface such that the sliding body 14 moves longitudinally with respect to the handle 12. In some embodiments, the interface comprises a rail, disposed on the handle 12, sliding body 14, or both. In some embodiments, the interface further includes a mating surface, to mate with the rail, which is disposed on the sliding body 14, handle 14, or both.

Although the delivery device 10 can be used with relatively long stents, it is not so limited. In this regard, it is capable of delivery shorter stents, as well. In some embodiments, the delivery device delivers stents between 40 mm and 100 mm in length. In some embodiments, however, the delivery device 10 can be used with even longer stents, for example iliac artery stents, that are 200 to 300 mm in length. As disclosed previously, depending upon the length of the stent to be deployed, the sliding body 14 can include any suitable number of flange portions 24. For example, in some embodiments, the sliding body 14 has three flange portions 24 that are all longitudinally offset from the others. In some embodiments, the sliding body 14 has four, five, or six flange portions 24 that are all longitudinally offset from the others. Further, where the sliding body 14 comprises a flange portion 24 on both sides (e.g., as shown in FIG. 1), the sliding body 14 comprises between 6 and 12 flange portions 24.

In some embodiments, the stent delivery device 10 further comprises a ratcheting mechanism along a portion of the handle 12 or sliding body 14, for example along the guide 18, to advance or lock the sliding body 14 in position. Further, in some embodiments, the stent delivery device 10 includes a lock to prevent movement of the sliding body 14 relative to the handle 12.

In some embodiments, a portion of the sliding body 14 or handle 12 is coated with a material to reduce or increase friction between the sliding components. In some embodiments, a material or coating having a high coefficient of friction is used to minimize unintended movement of the sliding body 14 relative to the handle 12. In some embodiments, such a material or coating includes an elastomeric material, silicone, or similar material.

In some embodiments, a slippery or hydrophilic coating can be applied to an inner surface of the sheath (not shown) and/or an outer surface of an inner tube (not shown) to reduce friction between the inner tube and sheath during deployment of the stent. Further, in some embodiments, a slippery or hydrophilic material can be applied to an outside surface of the sheath (not shown) to reduce friction between the sheath and the duct or vessel in which the sheath is being deployed.

In some embodiments, the stent delivery device 10 has markings (not shown) on the handle 12 to indicate the extent to which the sliding body 14 has been retracted.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A stent delivery device comprising:
a handle having a grip, a guide, and a cavity, the guide extending along an inner surface of the cavity; and
a sliding body comprising a body portion defining a longitudinal axis, the sliding body having a plurality of flange portions spaced apart longitudinally and fixed to the body portion, wherein the sliding body is slidable on the guide along the longitudinal axis to a position in which at least a portion of the sliding body including at least one flange portion is disposed within the cavity of the handle.

2. The stent delivery device of claim 1, wherein the guide defines a channel and the sliding body comprises a ridge slidable within the channel.

3. The stent delivery device of claim 1 wherein the guide comprises a ridge and the sliding body defines a channel, the ridge slidable within the channel.

4. The stent delivery device of claim 1, wherein the handle comprises a first guide and a second guide and the sliding body comprises a first ridge and a second ridge, the first ridge slidably engaged to the first guide and the second ridge slidably engaged to the second guide.

5. The stent delivery device of claim 4, wherein the first ridge is opposite the second ridge.

6. The stent delivery device of claim 1, wherein the handle further comprises a protruding member, the sliding body defines a cavity, the protruding member is insertable into the cavity, and the sliding body is slidable over the protruding member.

7. The stent delivery device of claim 6, wherein the protruding member defines a hole extending therethrough.

8. The stent delivery device of claim 1, wherein the plurality of flange portions includes first and second flanges, wherein movement of either the first or second flange relative to the handle causes the sliding body to slide relative to the handle.

9. The stent delivery device of claim 8, further comprising a third flange fixed to the body portion and a fourth flange fixed to the body portion, wherein the third and fourth flanges are longitudinally offset from one another along the longitudinal axis.

10. The stent delivery device of claim 9, wherein the first and third flanges extend from opposite sides of the body portion, and the second and fourth flanges extend from opposite sides of the body portion.

11. A delivery device for delivering a medical implant, the delivery device comprising:
a handle having a main body defining a cavity, a grip, and a guide extending outward from the main body; and
a sliding body slidable along the guide, the sliding body comprising a body portion defining a longitudinal axis and a plurality of flanges fixed to the body portion, wherein the plurality of flanges are longitudinally offset from one another by a fixed distance along the longitudinal axis, wherein the sliding body is slidable along the longitudinal axis to a position in which at least a portion of the sliding body and at least one flange is disposed within the cavity.

12. The delivery device of claim 11, wherein the handle further comprises a protruding member, the sliding body defines a cavity, the protruding member is insertable into the sliding body cavity, and the sliding body is slidable over the protruding member.

13. The delivery device of claim 12, wherein the protruding member defines a first hole extending therethrough.

14. The delivery device of claim 13, wherein the sliding body defines a second hole extending therethrough, the first and second holes centered about the longitudinal axis.

15. The delivery device of claim 11, wherein the guide includes first and second arms extending from the main body, wherein the sliding body is slidably positioned between the first and second arms.

16. The delivery device of claim 15, wherein each of the first and second arms defines a channel and the sliding body comprises two ridges, the ridges slidable along the channels.

17. The delivery device of claim 11, wherein the plurality of flanges includes first and second flanges, wherein movement of either the first or second flange relative to the handle causes the sliding body to slide relative to the handle.

18. The delivery device of claim 17, further comprising a third flange fixed to the body portion and a fourth flange fixed to the body portion, wherein the first and third flanges extend from opposite sides of the body portion, and the second and fourth flanges extend from opposite sides of the body portion.

19. A method of delivering a stent, the method comprising:
inserting a stent delivery catheter containing a stent and a stent sheath disposed over the stent, to a desired location within a patient;
attaching the stent sheath to a stent delivery device, the stent delivery device including a handle and a sliding body, the handle having a grip, a guide, and a cavity, the guide extending along an inner surface of the cavity, the sliding body comprising a body portion defining a longitudinal axis, the sliding body having a plurality of flange portions spaced apart longitudinally and fixed to the body portion, wherein the sliding body is slidable on the guide along the longitudinal axis to a first position in which at least a portion of the sliding body is disposed within the cavity of the handle, wherein the stent sheath is attached to the sliding body;
sliding the sliding body to the first position, thereby retracting the stent sheath from a portion of the stent; and
sliding the sliding body a second position in which a majority of the sliding body and at least one of the plurality of flanges are disposed within the cavity of the handle, thereby fully retracting the stent sheath from an entirety of the stent.

* * * * *